(12) United States Patent
Papathanassiu

(10) Patent No.: US 10,941,109 B2
(45) Date of Patent: Mar. 9, 2021

(54) COMPOSITIONS AND METHODS OF TREATMENT USING A BCAT1 INHIBITOR

(71) Applicant: Ergon Pharmaceuticals, LLC, Silver Spring, MD (US)

(72) Inventor: Adonia E. Papathanassiu, Washington, DC (US)

(73) Assignee: ERGON PHARMACEUTICALS LLC, Silver Springs, MD (US)

( * ) Notice: Subject to any disclaimer, the term of this patent is extended or adjusted under 35 U.S.C. 154(b) by 0 days.

(21) Appl. No.: 15/243,428

(22) Filed: Aug. 22, 2016

(65) Prior Publication Data

US 2016/0368862 A1    Dec. 22, 2016

Related U.S. Application Data

(63) Continuation-in-part of application No. 14/125,687, filed as application No. PCT/US2012/042046 on Jun. 12, 2012, now Pat. No. 9,422,224.

(60) Provisional application No. 61/520,645, filed on Jun. 13, 2011.

(51) Int. Cl.
*C07C 255/21*     (2006.01)
*C07C 59/84*      (2006.01)

(52) U.S. Cl.
CPC ............ *C07C 255/21* (2013.01); *C07C 59/84* (2013.01)

(58) Field of Classification Search
CPC ............................. C07C 255/21; C07C 59/84
See application file for complete search history.

(56) References Cited

U.S. PATENT DOCUMENTS

| | | |
|---|---|---|
| 2010/0286266 A1 | 11/2010 | Greig et al. |
| 2011/0093962 A1 | 4/2011 | Heidbrink et al. |

FOREIGN PATENT DOCUMENTS

| | | | |
|---|---|---|---|
| WO | WO96/15096 * | 5/1996 | ............ C07C 59/88 |
| WO | 01/42191 | 6/2001 | |
| WO | 02/24672 | 3/2002 | |
| WO | 2005/112633 | 12/2005 | |
| WO | 2010/127452 | 11/2010 | |
| WO | 2012/100957 | 8/2012 | |
| WO | 2012/173987 A2 | 12/2012 | |
| WO | 2012/173987 A3 | 12/2012 | |

OTHER PUBLICATIONS

Bartzatt et al (Anti-Inflammatory & Anti-Allergy Agents in Medicinal Chemistry, 2014, 13, 17-28).*
Patani et al., Bioisosterism: A Rational Approach in Drug Design, Chem. Rev. 1996, 96, 3147-3176.*
Burger, Isosterism and bioisosterism in drug design, p. 287-328, in Progress in Drug Research, vol. 37, 1991.*
Sarkisyan et al (Armyanskii Khimicheskii Zhurnal (1970), 23(5), 431-6) (Year: 1970).*
Metz et al (Synthesis (1980), (5), 394-7). (Year: 1980).*
Parameswara et al (Journal of the Chemical Society, Perkin Transactions 1: Organic and Bio-Organic Chemistry (1981), (10), 2662-5) (Year: 1981).*
Office Action dated Mar. 22, 2016 in corresponding Japanese Application No. 2014-515915, with English Translation.
PubChem (https://pubchem.ncbi.nlm.nih.gov/compound/hexanoic_acid#section=Top, accessed Apr. 18, 2016).
Bradley, J.R. TNF-mediated inflammatory disease. J. Pathol. (2008) 214(2): 149-60.
Lapadula, G. et al. Adalimumab in the treatment of immune-mediated diseases. Int J Immunopathol Pharmacol. (2014) 27(1 Suppl): 33-48.
Uppal, S.S., Hayat, S.J. and R. Raghupathy. Efficacy and safety of infliximab in active SLE: a pilot study. Lupus (2009)18(8): 690-7.
Chatzantoni, K. and A. Mouzaki. Anti-TNFα antibody therapies in autoimmune diseases. Curr. Top. Med. Chem. (2006) 6: 1707-1714.
Resende, A.L. et al.: "Bone Disease in Newly Diagnosed Lupus Nephritis Patients", Plos One, 9(9): 1-10 (2009).
Kurban, S. et al.: "Receptor activator of nuclear factor kappaB ligand (RANKL) and osteoprotegerin levels in multiple sclerosis", Multiple Sclerosis, 00: 1-2(2008).
Toberer, F. et al.: "Tissue microarray analysis of RANKL in cutaneous lupus erythematosus and psoriasis", Experimental Dermatology, 20: 601-602 (2011).
Takayanagi, H. et al.: "Involvement of receptor activator of nuclear factor kB ligand/osteoclast differentiation factor in osteoclastogenesis from synoviocytes in rheumatoid arthritis", Arthritis & Rheumatism, 43(2): 259-269(2000).
Walsh, M. et al.:"Biology of the RANKL-RANK-OPG system in immunity, bone and beyond", Frontiers in Immunology, 5(511): 1-11(2014).
Kim et al.: "Atorvastatin inhibits osteoclastogenesis by decreasing the expression of RANKL in the synoviocytes of rheumatoid arthritis, Arthritis Research & Therapy", 14(R187): 1-9(2012).
PubChem, http://pubchem.ncbi.nlm.nih.gov/compound/796813?from=summary, accessed Dec. 10, 2014.
Holloway, C. et al.: "Direct Enantioselective Brønsted Acid Catalyzed N-Acyliminium Cyclization Cascades of Tryptamines and Ketoacids", Organic Letters, 12(21): 4720-4723(2010).
Boers, R. et al., Synthesis and Spectroscopic Characterization of [5-13C]-and [6-13C]-Ubiquinone-10 for Studies of Bacterial Photosynthetic Reaction Centers, European Journal of Organic Chemistry, 2002 (1), pp. 189-202.
International Search Report for PCT/US2012/042046 dated Jan. 29, 2013.
Supplemental European Search Report in European Appln. No. 12 80 0655, dated Oct. 17, 2014.
English Translation of Japanese Office Action, dated Jul. 11, 2017, in corresponding Japanese Patent Application No. 2016-228528.
Bertocchio et al., "Reduction et cyclisation des esters et des acides δ-centoniques", Bulletin de la Societe Chimique de France, vol. 5, pp. 60-63 (1964).

(Continued)

*Primary Examiner* — Yong S. Chong
(74) *Attorney, Agent, or Firm* — Wenderoth, Lind & Ponack, LLP

(57) ABSTRACT

The present invention is directed to compounds and methods that inhibit the cytosolic form of BCAT1.

8 Claims, 1 Drawing Sheet

(56) References Cited

OTHER PUBLICATIONS

Lechevallier et al., "Etude des Petits Cycles-XLIV—Une voie de synthese des acyl-2 cyclobutanones", Tetrahedron, 39 (20): 3329-3336 (1983).
Extended European Search Report dated Nov. 22, 2017 in European Application No. 17187321.9.
Metz et al., "Intramolecular Cyclocondensation of 4- and 5-Oxocarboxylic Acids to Five- and Six-Membered Ring Systems", Synthesis, vol. 5, pp. 394-397 (1980).
Brown et al., "Enantioselective Oxidative Rearrangements with Chiral Hypervalent Iodine Reagents", Chem. Eur. J. 22(12): 4030-4035 (2016).
Amat et al., "Dynamic Kinetic Resolution and Desymmetrization Processes: A Straightforward Methodology for the Enantioselective Synthesis of Piperidines", Chem. Eur. J. 12(39): 7872-7881 (2006).
Gopinath et al., "As many as six tandem reactions in one step! Unprecedented formation of highly functionalized benzothiophenes", Chemical Communications, pp. 7131-7133 (2009).
Sarkisyan et al., "Synthesis of 3-methyl-5-substituted.5, 5-carbethoxyethan-2-one and transformation thereof", Armyanskii Khimicheskii Zhurnal, 23(5): 431-436 (1970).

* cited by examiner

COMPOSITIONS AND METHODS OF TREATMENT USING A BCAT1 INHIBITOR

FIELD OF THE INVENTION

The invention relates to compounds which are inhibitors of the branched-chain amino acid aminotransferase 1 (BCAT1) and to said compounds for use in therapy, to pharmaceutical compositions comprising said compounds, to methods of treating BCAT1-mediated diseases comprising administering to a patient in need thereof an effective amount of said compounds, and to the use of said compounds in the manufacture of medicaments.

BACKGROUND OF THE INVENTION

BCAT is the enzyme responsible for catalyzing the first step in the metabolism of branched-chain amino acids (BCAAs) such as leucine, isoleucine, and valine. The step involves the reversible transamination of BCAAs to corresponding branched-chain α-keto acids (BCKAs). BCAT exists in two forms: a cytosolic form (BCAT1) and a mitochondrial form (BCAT2). The two isozymes exhibit distinct and non-overlapping distribution. While BCAT2 is considered ubiquitous, BCAT1 has limited expression and is thought to be found only in embryonic tissues, in adult brain, ovary, and placenta and under certain pathological conditions such as hepatocellular carcinoma (Zheng, Y H et al. BCAT1, A Key Prognostic Predictor of Hepatocellular Carcinoma, Promotes Cell Proliferation and Induces Chemoresistance to Cisplatin, Liver Int. 2016 doi: 10.1111/liv.13178), lung cancer (Diaz-Lagares, A. et al. A Novel Epigenetic Signature for Early Diagnosis in Lung Cancer, Clin Cancer Res 2016, 22(13):3361-71), nasopharyngeal carcinoma (Zhou, W. et al. Over-expression of BCAT1, a c-Myc Target Gene, Induces Cell Proliferation, Migration and Invasion in Nasopharyngeal Carcinoma, Mol Cancer 2013, 12:53), ovarian cancer (Wang, Z Q et al. BCAT1 Expression Associates with Ovarian Cancer Progression: Possible Implications in Altered Disease Metabolism, Oncotarget 2015, 6(31):31522-43), breast cancer (Oktyabri, D. et al. DOT1L Histone Methyltransferase regulates the expression of BCAT1 and in involved in sphere formation and cell migration of breast cancer cell lines, Biochimie 2016, 123: 20-31), colon cancer (Pedersen, S K et al. Evaluation of an Assay for Methylated BCAT1 and IKZF1 in Plasma for Detection of Colorectal Neoplasia, BMC Cancer 2015, 15:654), and urothelial cancer (Chang, I W et al. BCAT1 Overexpression is an Indicator of Poor Prognosis in Patients with Urothelial Carcinomas of the Upper Urinary Track and Urinary Bladder, Histopathology 2016, 68(4):520-32). In addition to cancer, neurodegenerative diseases such as Alzheimer's disease express elevated levels of BCAT1 (Hull, J. et al., Regional Increase in the Expression of the BCAT proteins in Alzheimer' Disease Brain: Implications in Glutamate Toxicity, J. Alzheimers Dis. 2015, 45(3):891-905).

Inflammation is the physiological response to injury and the process by which the body protects itself against infection with foreign organisms such as bacteria and viruses. Excessive inflammation is associated with pathogenesis and can lead to disability and death such as in the case of autoimmune diseases and sepsis. BCAT1 disregulation has been implicated in some inflammatory disorders (Papathanassiu, A, Inhibition of branched chain amino acid aminotransferase 1 suppresses the severity of collagen-induced anrthritis, Journal of Immunology 2015, 194(1 Supplement) 139-7). Autoimmune diseases are conditions arising from the immune response of the body against its own substances, cells, and tissues; they are characterized by a chronic elevation of pro-inflammatory cytokines such as tumor necrosis factor-alpha (TNF-α), interleukin-1β (IL-1β), interleukin-6 (IL-6), interleukin-10 (IL-10), and interferon-alpha (IFN-α), which may also play a role in the pathogenesis of autoimmunity (Postal M, Appenzeller S, The role of tumor necrosis factor-alpha (TNF-α) in the pathogenesis of systemic lupus erythematosus, Cytokine (2011) 56:537-543). On the other hand, the uncontrollable release of the same cytokines as a result of an infection can activate the immune and coagulation systems in the body and trigger organ dysfunction and septic shock.

Immune tolerance is described as the lack of an immune response towards an antigen. If the antigen is a natural one, then this tolerance is called self-tolerance. Self-tolerance is lost in the case of autoimmune diseases. Other types of tolerance include allograft tolerance and fetomaternal tolerance. Allograft tolerance is described as the absence of a damaging immune response to a transplanted tissue in the absence of immunosuppression.

Collagen, especially type I collagen, is the most abundant protein in the human body and is found in all connective tissues. Its abundance has been attributed to its slow turnover rather to its high synthesis rate, which is slower than that of other abundant proteins (Wang H and Stefanovic B, Role of LARP6 and nonmuscle myosin in partitioning of collagen mRNAs to the ER membrane, PLoS ONE (2014) 9(10): e108870, 1:14). However, under certain pathological conditions such as reparative or reactive fibrosis, the rate of collagen synthesis increases several fold. In those conditions, collagen upregulation is commonly mediated by TGF-β$_1$, an important cytokine released by inflammatory cells, fibroblasts, and epithelial cells in response to various acute and chronic stimuli such as infections, toxins, and various types of injury. Uncontrolled collagen deposition by myofibroblasts and other cells in an organ or tissue is undesired as it gives rise to fibrosis and may result in the destruction of the architecture of the underlying organ or tissue. Subsequently, fibroproliferative disorders are a leading cause for morbidity and mortality.

SUMMARY OF THE INVENTION

In a first embodiment, the present invention provides BCAT1 inhibitors. The BCAT1 inhibitors of the invention include, in part, compounds encompassed by Formula (1):

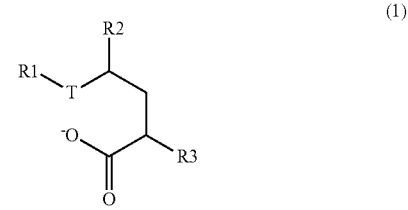

or an N-oxide thereof, or a pharmaceutically acceptable salt of the compound or N-oxide, wherein:

T is selected from the group consisting of —C(=O)— or —C(=NH)—,

R1 and R2 are independently selected from the group consisting of $C_1$-$C_6$ alkyl, $C_2$-$C_6$ alkenyl, $C_2$-$C_6$ alkynyl, $C_3$-$C_{14}$ cycloalkyl, aryl, heteroaryl, aryl($C_1$-$C_6$ alkyl), —CN, amino, ($C_1$-$C_6$)alkylamino, dialkyl($C_1$-$C_6$)amino, haloalkyl($C_1$-$C_6$), ($C_1$-$C_6$)alkoxy, ($C_1$-$C_6$) haloalkoxy, heteroaryl($C_1$-$C_6$ alkyl), ($C_4$-$C_{15}$)heterocyclic, ($C_4$-$C_{15}$)heterocyclic($C_1$-$C_6$ alkyl), $C_3$-$C_7$ cycloalkoxy, $C_6$-$C_{10}$-aryloxy, and the moieties (a-1), (a-2), and (a-3), wherein said alkyl, aryl, cycloalkyl, heterocyclic, heteroaryl, alkoxy, cycloalkoxy, haloalkyl, or haloalkoxy is further optionally substituted with one or more substituents selected from the group consisting of —$C_1$-$C_6$ alkyl, halo, CN, $CF_3$, —COOH, —OH, —$C_1$-$C_6$ alkoxy, —$NH_2$, —($C_1$-$C_6$ alkyl)$NH_2$, —($C_1$-$C_6$ alkyl)NH($C_1$-$C_6$ alkyl), —($C_1$-$C_6$ alkyl)N($C_1$-$C_6$ alkyl)$_2$, —NH($C_1$-$C_6$ alkyl), —N($C_1$-$C_6$ alkyl)$_2$, —$CONH_2$, —NH(CO)($C_1$-$C_6$ alkyl), —N($C_1$-$C_6$ alkyl)CO($C_1$-$C_6$ alkyl), —$SO_2$—($C_1$-$C_6$ alkyl), and —(SO)$NH_2$, R3 is selected from the group consisting of hydrogen, deuterium, $C_1$-$C_6$ alkyl, $C_2$-$C_6$ alkenyl, $C_2$-$C_6$ alkynyl, $C_3$-$C_{14}$ cycloalkyl, aryl, heteroaryl, aryl($C_1$-$C_6$ alkyl), —CN, amino, ($C_1$-$C_6$)alkylamino, dialkyl($C_1$-$C_6$) amino, haloalkyl($C_1$-$C_6$), ($C_1$-$C_6$)alkoxy, ($C_1$-$C_6$)haloalkoxy, heteroaryl($C_1$-$C_6$ alkyl), ($C_4$-$C_{15}$)heterocyclic, ($C_4$-$C_{15}$)heterocyclic($C_1$-$C_6$ alkyl), $C_3$-$C_7$ cycloalkoxy, $C_6$-$C_{10}$-aryloxy, and the moieties (a-1), (a-2), and (a-3), wherein said alkyl, aryl, cycloalkyl, heterocyclic, heteroaryl, alkoxy, cycloalkoxy, haloalkyl, or haloalkoxy is further optionally substituted with one or more substituents selected from the group consisting of $C_1$-$C_6$ alkyl, halo, CN, $CF_3$, —COOH, —OH, $C_1$-$C_6$ alkoxy, —$NH_2$, —($C_1$-$C_6$ alkyl)$NH_2$, —($C_1$-$C_6$ alkyl)NH($C_1$-$C_6$ alkyl), —($C_1$-$C_6$ alkyl)N($C_1$-$C_6$ alkyl)$_2$, —NH($C_1$-$C_6$ alkyl), —N($C_1$-$C_6$ alkyl)$_2$, —$CONH_2$, —NH(CO)($C_1$-$C_6$ alkyl), —N($C_1$-$C_6$ alkyl)CO($C_1$-$C_6$ alkyl), —$SO_2$—($C_1$-$C_6$ alkyl), and —(SO)$NH_2$,

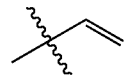
(a-1)

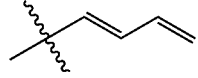
(a-2)

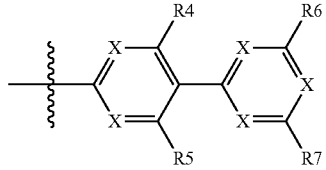
(a-3)

X is either N or CR8, and

R4, R5, R6, R7, and R8 are independently selected from the group consisting of hydrogen, deuterium, $C_1$-$C_6$ alkyl, $C_2$-$C_6$ alkenyl, $C_2$-$C_6$ alkynyl, $C_3$-$C_{14}$ cycloalkyl, aryl, heteroaryl, aryl($C_1$-$C_6$ alkyl), —CN, amino, ($C_1$-$C_6$)alkylamino, dialkyl($C_1$-$C_6$)amino, haloalkyl($C_1$-$C_6$), ($C_1$-$C_6$)alkoxy, ($C_1$-$C_6$)haloalkoxy, heteroaryl($C_1$-$C_6$ alkyl), ($C_4$-$C_{15}$)heterocyclic, ($C_4$-$C_{15}$)heterocyclic ($C_1$-$C_6$ alkyl), $C_3$-$C_7$ cycloalkoxy, $C_6$-$C_{10}$-aryloxy, wherein said alkyl, aryl, cycloalkyl, heterocyclic, heteroaryl, alkoxy, cycloalkoxy, haloalkyl, or haloalkoxy is further optionally substituted with one or more substituents selected from the group consisting of $C_1$-$C_6$ alkyl, halo, CN, $CF_3$, —COOH, —OH, $C_1$-$C_6$ alkoxy, —$NH_2$, —($C_1$-$C_6$ alkyl)$NH_2$, —($C_1$-$C_6$ alkyl) NH($C_1$-$C_6$ alkyl), —($C_1$-$C_6$ alkyl)N($C_1$-$C_6$ alkyl)$_2$, —NH($C_1$-$C_6$ alkyl), —N($C_1$-$C_6$ alkyl)$_2$, —$CONH_2$, —NH(CO)($C_1$-$C_6$ alkyl), —N($C_1$-$C_6$ alkyl)CO($C_1$-$C_6$ alkyl), —$SO_2$—($C_1$-$C_6$ alkyl), and —(SO)$NH_2$.

In some embodiments, T is a carbonyl group, R1 is $CF_3$ or $C_2$-$C_6$ alkyl, R2 is a aryl substituted with one or more substituents selected from the group consisting of $C_1$-$C_6$ alkyl, halo, CN, —COOH, —OH, $C_1$-$C_6$ alkoxy, —$NH_2$, —($C_1$-$C_6$ alkyl)$NH_2$, —($C_1$-$C_6$ alkyl)NH($C_1$-$C_6$ alkyl), —($C_1$-$C_6$ alkyl)N($C_1$-$C_6$ alkyl)$_2$, —NH($C_1$-$C_6$ alkyl), —N($C_1$-$C_6$ alkyl)$_2$, —$CONH_2$, —NH(CO)($C_1$-$C_6$ alkyl), —N($C_1$-$C_6$ alkyl)CO($C_1$-$C_6$ alkyl), and R3 is hydrogen.

In some embodiments, T is a carbonyl group, R1 is of $CF_3$ or $C_2$-$C_6$ alkyl, R2 is a heteroaryl substituted with one or more substituents selected from the group consisting of $C_1$-$C_6$ alkyl, halo, CN, —COOH, —OH, $C_1$-$C_6$ alkoxy, —$NH_2$, —($C_1$-$C_6$ alkyl)$NH_2$, —($C_1$-$C_6$ alkyl)NH($C_1$-$C_6$ alkyl), —($C_1$-$C_6$ alkyl)N($C_1$-$C_6$ alkyl)$_2$, —NH($C_1$-$C_6$ alkyl), —N($C_1$-$C_6$ alkyl)$_2$, —$CONH_2$, —NH(CO)($C_1$-$C_6$ alkyl), —N($C_1$-$C_6$ alkyl)CO($C_1$-$C_6$ alkyl), and R3 is hydrogen.

In some embodiments, T is a carbonyl group, R1 is an aryl substituted with one or more substituents selected from the group consisting of $C_1$-$C_6$ alkyl, halo, CN, —COOH, —OH, $C_1$-$C_6$ alkoxy, —$NH_2$, —($C_1$-$C_6$ alkyl)$NH_2$, —($C_1$-$C_6$ alkyl) NH($C_1$-$C_6$ alkyl), —($C_1$-$C_6$ alkyl)N($C_1$-$C_6$ alkyl)$_2$, —NH ($C_1$-$C_6$ alkyl), —N($C_1$-$C_6$ alkyl)$_2$, —$CONH_2$, —NH(CO) ($C_1$-$C_6$ alkyl), and —N($C_1$-$C_6$ alkyl)CO($C_1$-$C_6$ alkyl), R2 is a $CF_3$ or $C_2$-$C_6$ alkyl, and R3 is hydrogen.

In some embodiments, T is a carbonyl group, R1 is a heteroaryl substituted with one or more substituents selected from the group consisting of $C_1$-$C_6$ alkyl, halo, CN, —COOH, —OH, $C_1$-$C_6$ alkoxy, —$NH_2$, —($C_1$-$C_6$ alkyl) $NH_2$, —($C_1$-$C_6$ alkyl)NH($C_1$-$C_6$ alkyl), —($C_1$-$C_6$ alkyl)N ($C_1$-$C_6$ alkyl)$_2$, —NH($C_1$-$C_6$ alkyl), —N($C_1$-$C_6$ alkyl)$_2$, —$CONH_2$, —NH(CO)($C_1$-$C_6$ alkyl), and —N($C_1$-$C_6$ alkyl) CO($C_1$-$C_6$ alkyl), R2 is a $CF_3$ or $C_2$-$C_6$ alkyl, and R3 is hydrogen.

In some embodiments, T is a carbonyl group, R1 is $CF_3$ or $C_2$-$C_6$ alkyl, R2 is —$CH_3$ or $CF_3$, and R3 is an alkyl($C_1$-$C_6$)aryl, where the aryl group is optionally substituted with one or more substituents selected from the group $C_1$-$C_6$ alkyl, halo, CN, —COOH, —OH, $C_1$-$C_6$ alkoxy, —$NH_2$, —($C_1$-$C_6$ alkyl)$NH_2$, —($C_1$-$C_6$ alkyl)NH($C_1$-$C_6$ alkyl), —($C_1$-$C_6$ alkyl)N($C_1$-$C_6$ alkyl)$_2$, —NH($C_1$-$C_6$ alkyl), —N($C_1$-$C_6$ alkyl)$_2$, —$CONH_2$, —NH(CO)($C_1$-$C_6$ alkyl), and —N($C_1$-$C_6$ alkyl)CO($C_1$-$C_6$ alkyl).

In some embodiments, T is a carbonyl group, R1 and R2 are each independently an aryl group, substituted with one or more substituents selected from the group $C_1$-$C_6$ alkyl, halo, CN, —COOH, —OH, $C_1$-$C_6$ alkoxy, —($C_1$-$C_6$ alkyl) $NH_2$, —($C_1$-$C_6$ alkyl)NH($C_1$-$C_6$ alkyl), —($C_1$-$C_6$ alkyl)N ($C_1$-$C_6$ alkyl)$_2$, —NH($C_1$-$C_6$ alkyl), —N($C_1$-$C_6$ alkyl)$_2$, —$CONH_2$, —NH(CO)($C_1$-$C_6$ alkyl), and —N($C_1$-$C_6$ alkyl) CO($C_1$-$C_6$ alkyl), and R3 is a hydrogen.

In some embodiments, the BCAT1 inhibitor of the invention is one of the following compounds:

2-benzyl-4-methyl-5-oxohexanoic acid—Compound (2),
2-benzyl-4-methyl-5-oxooct-7-enoic acid—Compound (3),
(6E,8E)-4-phenyl-5-oxodeca-6,8-dienoic acid—Compound (4),
5-{[1,1'-biphenyl]-4-yl}-4-methyl-5-oxopentanoic acid—Compound (5),
4-methyl-5-oxo-5-phenylpentanoic acid—Compound (6),
5-oxo-4-phenylhexanoic acid—Compound (7),
2-(2-cyanoethyl)-4-methyl-5-oxohexanoic acid—Compound (8), 5-oxo-4-(2,4,6-trimethylphenyl)heptanoic acid—Compound (9), 4-(4-amino-2,6-dimethylphenyl)-5-oxo-heptanoic acid—Compound (10), 4-[2-methyl-4-(trifluromethyl)phenyl]-5-oxoheptanoic acid—Compound (11), (6E,8E)-4-(4-aminophenyl)-5-oxodeca-6,8-dienoic acid—Compound (12), 5-{4'-(dimethylamino)-[1,1'-biphenyl]-4-yl}-4-methyl-5-oxopentanoic acid—Compound (13), 5-{4'methoxy-2',6'-dimethyl-[1,1'-biphenyl]-4-yl}-4-methyl-5-oxophentanoic acid—Compound (14), and 4-[4-(trifluromethyl)benzoyl]hex-5-enoic acid—Compound (15).

Compound (2)
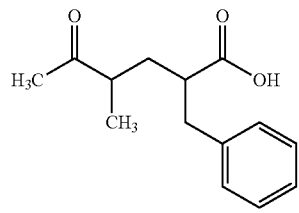

Compound (3)
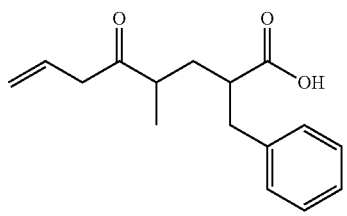

Compound (4)
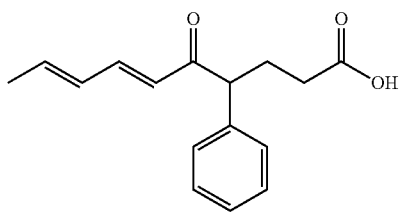

Compound (5)
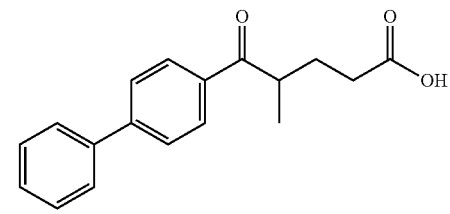

Compound (6)
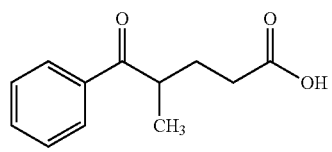

Compound (7)
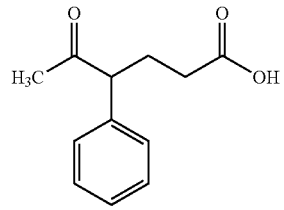

Compound (8)
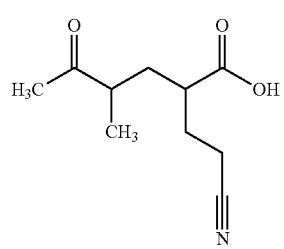

In a second embodiment, the present invention provides methods for treating a BCAT1-mediated (or BCAT1-associated) disorder or disease in a subject (e.g. a mammal such as a human). The method comprises administering to a subject in need thereof a therapeutically effective amount of one or more compounds of Formula (1) or an N-oxide thereof or a pharmaceutically acceptable salt of the compound or the N-oxide (including all embodiments and combinations of two or more embodiments described herein or any subcombination thereof). In certain aspects, the methods are practiced using one or more of Compounds (2)-(15). In certain aspects, the disease is characterized by collagen deposition, including excessive collagen deposition. In certain aspects, the collagen deposition disease is associated with fibrosis, such as, but not limited to, fibrosis of the lung, fibrosis of the liver, fibrosis of the kidney, fibrosis of the eye, fibrosis for the bone marrow, fibrosis of the spleen, fibrosis of the intestine, fibrosis of the joints, laryngeal fibrosis, fibrosis of the vocal chords, restenosis-related vascular fibrosis and post-transplantation fibrosis.

In a third embodiment, the present invention provides the use of one or more compounds of Formula (1) or an N-oxide thereof or a pharmaceutically acceptable salt of the compound or the N-oxide (including all embodiments and combinations of two or more embodiments described herein or any subcombination thereof) in the manufacture a medicament for use in treating an BCAT1-mediated (or BCAT1-associated) disorder or disease as described herein. In certain aspects, the use is made of one or more of Compounds (2)-(15).

BCAT1-mediated (or BCAT1-associated) disorders and diseases include, for example, cancers, autoimmune diseases, sepsis, induction of allograft tolerance, fibrosis, and neurodegenerative diseases.

BRIEF DESCRIPTION OF THE TABLES

TABLE 1 shows inhibition of BCAT1 enzymatic activity by various compounds of Formula (1).

TABLE 2 shows inhibition of collagen I production from TGF-$\beta_1$-stimulated human fibroblasts after treatment with various compounds of Formula (1).

DETAILED DESCRIPTION OF THE INVENTION

Figures 1A, 1B:
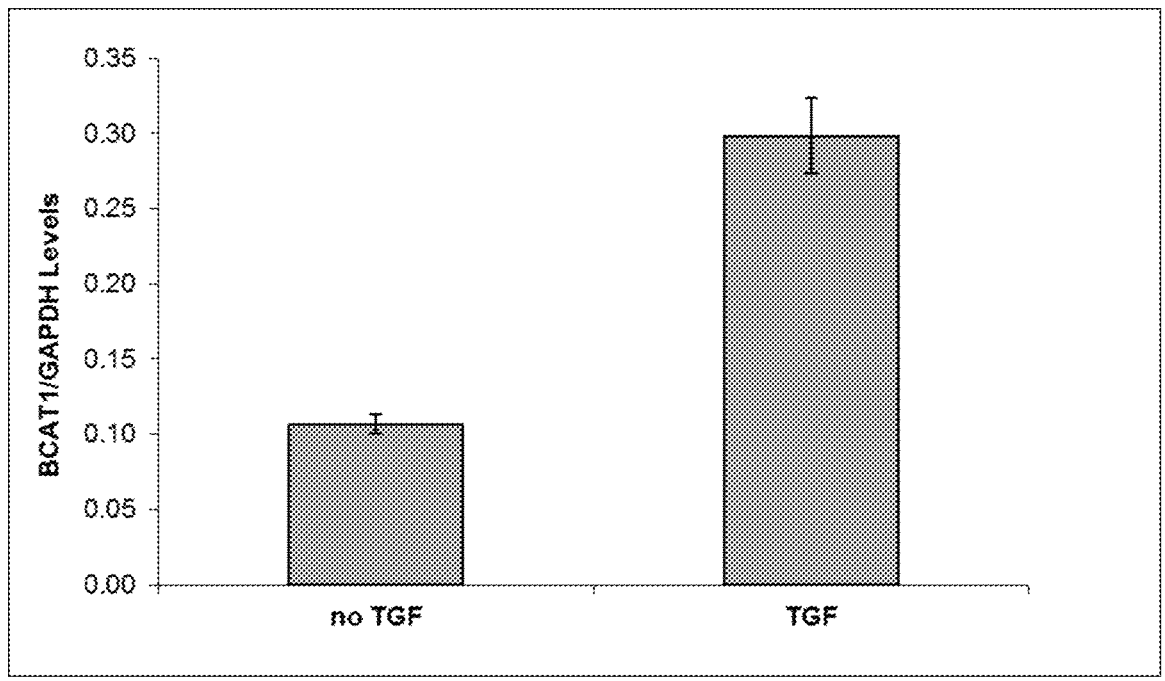
FIG. 1A shows upregulation of BCAT1 expression in human fibroblasts after stimulation of the cells with TGF-$\beta_1$ as determined by Western immunoblotting.
FIG. 1B shows normalized BCAT1 expression levels in unstimulated and TGF-$\beta_1$-stimulated human fibroblasts as determined from 4 different experiments using Western immunoblotting.

Other objects, features and aspects of the present invention are disclosed in, or are obvious from, the following Detailed Description. It is to be understood by one of ordinary skill in the art that the present discussion is a description of exemplary embodiments only and is not intended as limiting the broader aspects of the present invention, which broader aspects are embodied in the exemplary construction.

The present invention comprises BCAT1 inhibitors, e.g., compounds of Formula (1). These compounds are suitable for the treatment of a human or animal suffering from a disorder or disease that is BCAT1-mediated (BCAT1-associated) including but not limited to cancer, an autoimmune disease, sepsis, a neurodegenerative disease, and a fibrotic disease.

I. Definitions

As used herein, the term "alkyl" is defined to include saturated aliphatic hydrocarbons including straight chains and branched chains. The term "$C_1$-$C_6$ alkyl," as well as the alkyl moieties of other groups referred to herein (i.e., $C_1$-$C_6$ alkoxy) refers to linear or branched radicals of 1 to 6 carbon atoms (i.e., methyl, ethyl, n-propyl, isopropyl, n-butyl, isobutyl, sec-butyl, terl-butyl, n-pentyl, or n-hexyl). An alkyl group can optionally be substituted by one or more (e.g., 1 to 5) suitable substituents.

As used herein, the term "alkenyl" refers to aliphatic hydrocarbons having at least one carbon-carbon double bond, including straight chains and branched chains having at least one carbon-carbon double bond. The term "$C_2$-$C_6$ alkenyl" means straight or branched chain unsaturated radicals (having at least one carbon-carbon double bond) of 2 to 6 carbon atoms, including, but not limited to, ethenyl, 1-propenyl, 2-propenyl (allyl), isopropenyl, 2-methyl-1-propenyl, 1-butenyl, 2-butenyl, and the like. An alkenyl group optionally can be substituted by one or more (e.g., 1 to 5) suitable substituents. When the compounds of Formula (1) contain an alkenyl group, the alkenyl group may exist as the pure trans-(E) form, the pure cis-(Z) form, or any mixture thereof.

As used herein, the term "alkynyl" refers to aliphatic hydrocarbons having at least one carbon-carbon triple bond, including straight chains and branched chains having at least one carbon-carbon triple bond. The term "$C_2$-$C_6$ alkynyl" refers to straight or branched hydrocarbon chain alkynyl radicals as defined above, having 2 to 6 carbon atoms. An alkynyl group optionally can be substituted by one or more (e.g. 1 to 5) suitable substituents.

As used herein, the term "cycloalkyl" refers to saturated or unsaturated, non-aromatic, monocyclic or polycyclic (such as bicyclic) hydrocarbon rings (e.g., monocyclics such as cyclopropyl, cyclobutyl, cyclopentyl, cyclohexyl, cycloheptyl, cyclooctyl, cyclononyl, or bicyclics including spiro, fused, or bridged systems (such as bicyclo[1.1.1]pentanyl, bicyclo[2.2.1]heptanyl, bicyclo[3.2.1]octanyl or bicyclo[5.2.0]nonanyl, decahydronaphthalenyl, etc.). The cycloalkyl group has 3 to 14 carbon atoms. In some embodiments the cycloalkyl may optionally contain one, two or more non-cumulative non-aromatic double or triple bonds and/or one to three oxo groups. In some embodiments, the bicycloalkyl group has 6 to 14 carbon atoms. For example, the term "$C_3$-$C_{14}$ cycloalkyl" refers to saturated or unsaturated, non-aromatic, monocyclic or polycyclic (such as bicyclic) hydrocarbon rings of 3 to 14 ring-forming carbon atoms (i.e., cyclopropyl, cyclobutyl, cyclopentyl, cyclohexyl, bicyclo[1.1.1]pentanyl, or cyclodecanyl); and the term "$C_3$-$C_7$ cycloalkyl" refers to saturated or unsaturated, non-aromatic, monocyclic or polycyclic (such as bicyclic) hydrocarbon rings of 3 to 7 ring-forming carbon atoms (i.e., cyclopropyl, cyclobutyl, cyclopentyl, cyclohexyl, bicyclo[1.1.1]pentan-1-yl, or bicyclo[1.1.1]pentan-2-yl).

As used herein, the term "aryl" refers to all-carbon monocyclic or fused-ring polycyclic aromatic groups having a conjugated pi-electron system. The aryl group has 6 to 10 carbon atoms in the ring(s). Most commonly, the aryl group has 6 carbon atoms in the ring. For example, as used herein, the term "aryl" means aromatic radicals containing from 6 to 10 carbon atoms such as phenyl or naphthyl. The aryl group optionally can be substituted by 1 or more (e.g., 1 to 5) suitable substituents.

As used herein, the term "heteroaryl" refers to monocyclic or fused-ring polycyclic aromatic heterocyclic groups with one or more heteroatom ring members (ring-forming atoms) each independently selected from O, S and N in at least one ring. The heteroaryl group has 5 to 14 ring-forming atoms, including 1 to 13 carbon atoms, and 1 to 8 heteroatoms selected from O, S and N. In some embodiments, the heteroaryl group has 5 to 10 ring-forming atoms including one to four heteroatoms. The heteroaryl group can also contain one to three oxo or thiono (i.e. =S) groups. In some embodiments, the heteroaryl group has 5 to 8 ring-forming atoms including one, two or three heteroatoms. For example, the term "5-membered heteroaryl" refers to a monocyclic heteroaryl group as defined above with 5 ring-forming atoms in the monocyclic heteroaryl ring; the term "6-membered heteroaryl" refers to a monocyclic heteroaryl group as defined above with 6 ring-forming atoms in the ring; and the term "5- or 6-membered heteroaryl" refers to a monocyclic heteroaryl group as defined above with 5 or 6 ring-forming atoms in the monocyclic heteroaryl ring. For another example, term "5- or 10-membered heteroaryl" refers to a monocyclic or bicyclic heteroaryl group as defined above with 5, 6, 7, 8, 9 or 10 ring-forming atoms in the monocyclic or bicyclic heteroaryl ring. A heteroaryl group optionally can be substituted by 1 or more (e.g., 1 to 5) suitable substituents. Examples of monocyclic heteroaryls include those with 5 ring-forming atoms including one to three heteroatoms or those with 6 ring-forming atoms including one, two or three nitrogen heteroatoms. Examples of fused bicyclic heteroaryls include two fused 5- and/or 6-membered monocyclic rings including one to four heteroatoms. Examples of heteroaryl groups include pyridinyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl (e.g., pyrazol-1-yl, pyrazol-3-yl, pyrazol-4-yl), tetrazolyl, triazolyl (e.g., 1,2,3-triazolyl, 1,2,4-triazolyl), oxadiazolyl (e.g., 1,2,3-oxadiazolyl), thiadiazolyl (i.e., 1,3,4-thiadiazolyl), quinolyl, isoquinolyl, benzothienyl, benzofuryl, indolyl, 1H-imidazo[4,5-c]pyridinyl, imidazo[1,2-a]pyridinyl, 1H-pyrrolo[3,2-c]pyridinyl, imidazo[1,2-a]pyrazinyl, imidazo[2,1-c][1,2,4]triazinyl, imidazo[1,5-a]pyrazinyl, imidazo[1,2-a]pyrimidinyl, 1H-indazolyl, 9H-purinyl, imidazo[1,2-a]pyrimidinyl, [1,2,4]triazolo[1,5-a]pyrimidinyl, [1,2,4]triazolo[4,3-b]pyridazinyl, isoxazolo[5,4-c]pyridazinyl, isoxazolo[3,4-c]

pyridazinyl, pyridone, pyrimidone, pyrazinone, pyrimidinone, 1H-imidazol-2(3H)-one, 1H-pyrrole-2,5-dione, 3-oxo-2H-pyridazinyl, 1H-2-oxo-pyrimidinyl, 1H-2-oxo-pyridinyl, 2,4(1H,3H)-dioxo-pyrimidinyl, 1H-2-oxo-pyrazinyl, and the like.

As used herein, the term "heterocycloalkyl" refers to a monocyclic or polycyclic (including 2 or more rings that are fused together, including spiro, fused, or bridged systems, for example, a bicyclic ring system), saturated or unsaturated, non-aromatic 4- to 15-membered ring system (such as a 4- to 14-membered ring system, 4- to 12-membered ring system, 5- to 10-membered ring system, 4- to 8-membered ring system, 4- to 6-membered ring system, or 5- to 6-membered ring system), including 1 to 14 ring-forming carbon atoms and 1 to 10 ring-forming heteroatoms each independently selected from O, S and N. The heterocycloalkyl group can also optionally contain one or more oxo or thiono (i.e. =S) groups. For example, the term "4- to 12-membered heterocycloalkyl" refers to a monocyclic or polycyclic, saturated or unsaturated, non-aromatic 4- to 12-membered ring system that comprises one or more ring-forming heteroatoms each independently selected from O, S and N and the term "4- to 10-membered heterocycloalkyl" refers to a monocyclic or polycyclic, saturated or unsaturated, non-aromatic 4- to 10-membered ring system that comprises one or more ring-forming heteroatoms each independently selected from O, S and N. For another example, the term "4- to 6-membered heterocycloalkyl" refers to a monocyclic or polycyclic, saturated or unsaturated, non-aromatic 4- to 6-membered ring system that comprises one or more ring-forming heteroatoms each independently selected from O, S and N, and the term "5- to 6-membered heterocycloalkyl" refers to a monocyclic or polycyclic, saturated or unsaturated, non-aromatic 5- to 6-membered ring system that comprises one or more ring-forming heteroatoms each independently selected from O, S and N. Also included in the definition of heterocycloalkyl are moieties that have one or more aromatic rings (including aryl and heteroaryl) fused to the non-aromatic heterocycloalkyl ring, for example pyridinyl, pyrimidinyl, thiophenyl, pyrazolyl, phthalimidyl, naphthalimidyl, and benzo derivatives of the nonaromatic heterocycloalkyl rings. The heterocycloalkyl group optionally can be substituted by 1 or more (e.g., 1 to 5) suitable substituents. Examples of such heterocycloalkyl rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydroth iazinyl, tetrahydroth iadiazinyl, morpholinyl, oxetanyl, tetrahydrodiazinyl, oxazinyl, oxathiazinyl, quinuclidinyl, chromanyl, isochromanyl, benzoxazinyl, 2-oxaspiro[3.3]heptyl {e.g. 2-oxaspiro[3.3]hept-6-yl}, 7-azabicyclo[2.2.1]heptan-1-yl, 7-azabicyclo[2.2.1]heptan-2-yl, 7-azabicyclo[2.2.1]heptan-7-yl, 2-azabicyclo[2.2.1]heptan-3-on-2-yl, 3-azabicyclo[3.1.0]hexanyl, 3-azabicyclo[4.1.0]heptanyl and the like. Further examples of heterocycloalkyl rings include tetrahydrofuran-2-yl, tetrahydrofuran-3-yl, tetrahydropyranyl (e.g. tetrahydro-2H-pyran-4-yl), imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, 1,4-oxazepan-1-yl, isothiazolidinyl, 1,3-thiazolidin-3-yl, 1,2-pyrazolidin-2-yl, 1,2-tetrahydrothiazin-2-yl, 1,3-thiazinan-3-yl, 1,2-tetrahydrodiazin-2-yl, 1,3-tetrahydrodiazin-1-yl, 1,4-oxazin-4-yl, oxazolidinonyl, 2-oxo-piperidinyl (e.g., 2-oxo-piperidin-1-yl), 2-oxoazepan-3-yl, and the like. Some examples of aromatic-fused heterocycloalkyl groups include indolinyl, isoindolinyl, isoindolin-1-one-3-yl, 5,7-dihydro-6H-pyrrolo[3,4-b]pyridin-6-yl, 6,7-dihydro-5H-pyrrolo[3,4-d]pyrimidin-6-yl, 4,5,6,7-tetrahydrothieno[2,3-c]pyridine-5-yl, 5,6-dihydrothieno[2,3-c]pyridin-7 (4H)-one-5-yl, 1,4,5,6-tetrahydropyrrolo[3,4-c]pyrazol-5-yl, and 3,4-dihydroisoquinolin-1 (2H)-one-3-yl groups. The heterocycloalkyl group is optionally substituted by 1 or more (e.g., 1 to 5) suitable substituents. Examples of heterocycloalkyl groups include 5- or 6-membered monocyclic rings and 9- or 10-membered fused bicyclic rings.

As used herein, the term "halo" or "halogen" group is defined to include fluorine, chlorine, bromine or iodine.

As used herein, the term "haloalkyl" refers to an alkyl group having one or more halogen substituents (up to perhaloalkyl, i.e., every hydrogen atom of the alkyl group has been replaced by a halogen atom). For example, the term "$C_1$-$C_6$ haloalkyl" refers to $C_1$-$C_6$ alkyl group having one or more halogen substituents (up to perhaloalkyl, i.e., every hydrogen atom of the alkyl group has been replaced by a halogen atom). Examples of haloalkyl groups include $CF_3$, $C_2F_5$, $CHF_2$, $CH_2F$, $CH_2CF_3$ and the like.

As used herein, the term "alkoxy" or "alkyloxy" refers to an —O-alkyl group. For example, the term "$C_1$-$C_6$ alkoxy" or "$C_1$-$C_6$ alkyloxy" refers to an —O—($C_1$-$C_6$ alkyl) group. Examples of alkoxy include methoxy, ethoxy, propoxy (i.e., n-propoxy and isopropoxy), terl-butoxy, and the like. The alkoxy or alkyloxy group optionally can be substituted by 1 or more (e.g., 1 to 5) suitable substituents.

As used here, the term "haloalkoxy" refers to an —O-haloalkyl group. For example, the term "$C_1$-$C_6$ haloalkoxy" refers to an —O—($C_1$-$C_6$ haloalkyl) group. An example of haloalkoxy is —$OCF_3$ or —$OCHF_2$.

As used herein, the term "cycloalkoxy" or "cycloalkyloxy" refers to an —O-cycloalkyl group. For example, the term "$C_3$-$C_7$ cycloalkoxy" or "$C_3$-$C_7$ cycloalkyloxy" refers to an —O— ($C_3$-$C_7$ cycloalkyl) group. Examples of cycloalkoxy include cyclopropoxy, cyclobutoxy, cyclopentoxy, cyclohexanoxy, and the like. The cycloalkoxy or cycloalkyloxy group optionally can be substituted by 1 or more (e.g., 1 to 5) suitable substituents.

As used here, the term "$C_6$-$C_{10}$ aryloxy" refers to an —O—($C_6$-$C_{10}$ aryl) group. An example of a $C_6$-$C_{10}$ aryloxy group is —O-phenyl [i.e., phenoxy]. The $C_6$-$C_{10}$ aryloxy group can optionally be substituted by 1 or more (e.g., 1 to 5) suitable substituents.

As used herein, the term "oxo" refers to =O. When an oxo is substituted on a carbon atom, they together form a carbonyl moiety [—C(=O)—]. When an oxo is substituted on a sulfur atom, they together form a sulfinyl moiety [—S(=O)—]; when two oxo groups are substituted on a sulfur atom, they together form a sulfonyl moiety [—S(=O)z—].

As used herein, the term "suitable salts" refers to non-toxic salts formed from the acid of Formula (1) and a base. Examples of bases include hydroxides of aluminium, zinc, calcium, magnesium, potassium, and sodium, amino acids such as arginine, glycine, and lysine, benzathine, choline, diethylamine, diolamine, meglumine, olamine, and tromethamine.

As used herein, the terms "BCAT1-mediated" and "BCAT1-associated" disorder or disease refer to disorder and diseases characterized by expression of BCAT1 or elevated BCAT1 enzymatic activity. Examples of such diseases are cancers, autoimmune diseases, neurodegenerative disease, allograft rejection, and fibrotic diseases.

As used herein, the term "$IC_{50}$" refers to the concentration of a compound needed to reduce a given biological response by 50%.

As used herein, the terms "treat", "treating" and "treatment" have their ordinary and customary meanings, and include one or more of, ameliorating a symptom of a disease, blocking or ameliorating a recurrence of a symptom of a disease, decreasing in severity and/or frequency a symptom of a disease. Treatment means ameliorating, blocking, reducing, decreasing or inhibiting by about 1% to about 100% versus a subject to which the treatment has not been administered. Preferably, the ameliorating, blocking, reducing, decreasing or inhibiting is about 100%, about 99%, about 98%, about 97%, about 96%, about 95%, about 90%, about 80%, about 70%, about 60%, about 50%, about 40%, about 30%, about 20%, about 10%, about 5% or about 1%. The treatment may begin prior to, concurrent with, or after the onset of clinical symptoms of the disease. Thus, the subject may have a disease or merely be susceptible to the disease. The results of the treatment may be permanent or may continue for a period of days (such as 1, 2, 3, 4, 5, 6 or 7 days), weeks (such as 1, 2, 3 or 4 weeks) or months (such as 1, 2, 3, 4, 5, 6 or more months).

The term "subject" is intended to mean an animal, such birds or mammals, including humans and animals of veterinary or agricultural importance, such as dogs, cats, horses, sheep, goats, and cattle.

Cancers for which the compounds of Formula (1), N-oxides thereof, and pharmaceutically acceptable salts of the foregoing of the invention may be useful in treating include acute lymphoblastic leukemia, acute myeloid leukemia, adrenocortical carcinoma, adrenal cortex cancer, anal, astrocytomas, atypical teratoid/phabdoid tumor, basal cell carcinoma, bile duct cancer, bladder cancer, bone cancer (including Ewing sarcoma and osteosarcoma, malignant fibrous histiocytoma), brain tumors (glioblastoma, astrocytoma, neuroblastoma), breast cancer, bronchial cancer, Burkitt lymphoma, gastrointestinal cancer, cardiac cancer, cancer of the central nervous system, cervical cancer, cholangiocarcinoma, chordoma, chronic lymphocytic leukemia, chronic myelogenous leukemia, chronic myeloproliferative neoplasms, colorectal cancer, craniopharyngioma, cutaneous T-cell lymphoma, ductal carcinoma in situ, endometrial cancer, esophageal cancer, extracranial germ tumor, extragonadal germ cell cancer, eye (intraocular, retinoblastoma) cancer, cancer of the fallopian tubes, cancer of the gallbladder, gastric (stomach) cancer, hairy cell leukemia, head and neck cancer, hepatocellular cancer, histiocytosis, Hodgkin Lymphoma, pancreatic cancer, Kaposi's sarcoma, kidney cancer, head and neck cancer, lung cancer, macroglobulinemia, skin cancer including melanomas, Merkell cell carcinoma, mesothelioma, multiple endocrine neoplasia syndromes, myelodysplastic syndromes, chronic myelogenous leukemia, acute myeloid leukemia, non-Hodgkin lymphoma, ovarian, pancreatic cancer, penile, pharyngeal, pituitary, rhabdomyosarcoma, salivary gland, small intestine cancer, soft tissue sarcoma, cutaneous T-cell lymphoma, testicular cancer, throat cancer, oral cavity, thymoma and thymic carcinoma, thyroid cancer, vaginal cancer, vascular tumors, vulvar cancer, and Wilms tumor.

Autoimmune diseases for which the compounds of Formula (1), N-oxides thereof, and pharmaceutically acceptable salts of the foregoing of the invention may be useful in treating include Type I or juvenile onset diabetes, rheumatoid arthritis, juvenile rheumatoid arthritis, Reiter's syndrome, systemic lupus erythematosus, Sjogren's syndrome, systemic sclerosis, autoimmune encephalomyelitis, Balo disease, Bickerstaff's encephalitis, anti-NMDA receptor encephalitis, chronic inflammatory demyelinating polyneuropathy, Guillain-Barre syndrome, idiopathic inflammatory demyelinating diseases, Lambert-Eaton myasthenic syndrome, multiple sclerosis, progressive inflammatory neuropathy, Stiff person syndrome, Sydenham chorea, polymyositis and dermatomyositis, bullous pemphigoid, autoimmune angioedema, autoimmune urticarial vasculitis, cicatricial pemphigoid, dermatitis herpetiformis, epidermolysis bullosa acquisita, erythema nodosum, hidradenitis suppurativa, Lichen planus, Lichen sclerosus, Pemphigus vulgaris, Mucha-Habermann disease, systemic scleroderma, Addison's disease, Hashimoto's thyroiditis, Graves' disease, membranous glomerulonephritis, Goodpasture's disease, interstitial cystitis, glanulomatosis, autoimmune enteropathy, Coeliac disease, Crohn's disease, ulcerative colitis, primary biliary cirrhosis, chronic aggressive hepatitis, autoimmune hepatitis, autoimmune metaplastic atrophic gastritis, autoimmune hemolytic anemia, autoimmune lymphoproliferative syndrome, autoimmune neutropenia, autoimmune thrombocytopenia, ankylosing spondylitis, Dercum's disease, adult-onset Still's disease, CREST syndrome, Felty syndrome, IgG4-related diseases, mixed connective tissue disease, relapsing polychondritis, retroperitoneal fibrosis, sarcoidosis, Schnitzler syndrome, myasthenia gravis, myositis, polymyositis, sympathetic ophthalmia, autoimmune retinopathy, autoimmune uveitis, Susac's syndrome, Cogan's syndrome, and autoimmune orchitis, autoimmune myocarditis, autoimmune cardiomyopathy, Coxsackie myocarditis, Dressler's syndrome, autoimmune angioedema, psoriasis, autoimmune polyendocrine syndrome Type 1, 2, and 3, autoimmune pancreatitis, autoimmune inner disease, Bahcet's disease, eosinophilic granulomatosis with polyangiitis, giant cell arteritis, vasculitis, IgA vasculitis, and Kawasaki's disease.

Instances of organ transplantation, i.e. induction of allograft tolerance, for which the compounds of Formula (1), N-oxides thereof, and pharmaceutically acceptable salts of the foregoing of the invention may be useful in treating through the induction of immune tolerance include transplantation of heart, heart-valve, lung, kidney, liver, pancreas, intestine, stomach, testis, hand, cornea, skin, face, islets of Langerhans, bone marrow, blood vessels, and, bone.

Instances of neurodegenerative diseases for which the compounds of Formula (1), N-oxides thereof, and pharmaceutically acceptable salts of the foregoing of the invention may be useful in treating include Alzheimer's disease, Parkinson's disease, Huntington's disease, amyotrophic lateral sclerosis, and Batten disease.

Instances of fibrotic diseases (i.e. fibrosis) for which the compounds of Formula (1), N-oxides thereof, and pharmaceutically acceptable salts of the foregoing of the invention may be useful in treating include fibrosis of the lung, kidney, liver, skin, eye, heart, bone, pancreas, peritoneal cavity, intestine, soft tissue of the mediastinum, spleen, joint, or vocal chords. Specifically, diseases characterized by lung fibrosis include but are not limited to interstitial lung diseases, idiopathic fibrosis and cystic fibrosis; diseases characterized by fibrosis of the kidney include but are not limited to tubulointerstitial fibrosis, IgA nethropathy, interstitial fibrosis/tubular atrophy, chronic kidney damage, glomerular disease, glomerulonephritis, diabetes mellitus nephropathy, idiopathy focal segmental glomerulosclerosis, membranous nephropathy, collapsing glomerulopathy, chronic kidney infection, and end stage renal disease; diseases characterized by fibrosis of the liver include but are not limited to chronic liver injury, hepatitis infection, non-alcoholic steatohepatitis, and cirrhosis; fibrosis of the skin includes but are not limited to scleroderma and keloid; diseases characterized by fibrosis of the eye include but are not limited to proliferative vitreoretinopathy (PVR), scarring resulting from surgery to treat cataract or macular degeneration, glaucoma, and Grave's ophthalmopathy; diseases characterized by fibrosis of the heart include but are not limited to endomyocardial fibrosis, old myocardial infarction, and hypertrophic obstructive cardiomyopathy; diseases characterized by fibrosis of the bone include but are not limited to myelofibrosis; diseases characterized by fibrosis of the intestine include but are not limited to Crohn's Disease; diseases characterized by fibrosis of the joints include but are not limited to arthrofibrosis; diseases characterized by fibrosis of the vocal chords include but are not limited to vocal cord scarring, vocal cord mucosal fibrosis, and laryngeal fibrosis. Other fibrotic diseases related to the present invention include but are not limited to restenosis-related vascular fibrosis and post-transplantation fibrosis.

Administration

The BCAT1 inhibitors of the invention may be used in the methods defined herein. Typically, the inhibitors will be formulated for in vivo methods and use. Formulations comprising the BCAT1 inhibitors, e.g., the compounds of Formula (I), may be administered to a subject in need thereof via one or more of topical, oral, rectal and parenteral (intravenous, subcutaneous or intramuscular) routes. The formulations may also be incorporated into biodegradable polymers for sustained release implanted at the disease site. The dosage of the formulations depends on the condition treated, the activity of the drug used, the route of administration, and other clinical factors such as severity of the disease and weight of the patient. The formulations are formulated in ways suitable for the specific route of administration.

Formulations suitable for oral administration include capsules, cachets or tablets containing a predetermined amount of the active ingredient, powder or granules, solutions, suspensions, and emulsions. Formulations suitable for topical administration in the mouth include lozenges, pastilles, and mouthwashes. Formulations suitable for topical administration to the skin include ointments, creams, gels, pastes, and transdermal patches. Formulations for rectal administration may be presented as a suppository with a suitable base, while vaginal administrations maybe presented as pessaries, tampons, creams, gels, pastes, foams, and sprays comprising the active ingredient in an appropriate carrier. Formulations suitable for parenteral administration include aqueous and non-aqueous sterile injection solutions presented in unit-dose or multi-dose containers. It should be also understood that, in addition to the ingredients mentioned above, formulations of this invention might include other agents conventional in the art having regard to the type of formulation in question.

In each of the embodiments of the invention directed to methods of treatment, the formulations may comprise one or more BCAT1 inhibitors alone or the formulations may further comprise a pharmaceutically acceptable excipient. Whether administered alone or in combination with an excipient, formulations comprising one or more BCAT1 inhibitors are administered to a subject in an amount which is effective for treating the specific disorder or disease. In general, formulations comprising one or more BCAT1 inhibitors are administered to a subject in an amount of from about 0.1 mg/kg to about 10 mg/kg body weight. Acceptable ranges also include: from about 0.1 mg/kg to about 10 mg/kg, 0.1 mg/kg to about 9 mg/kg, 0.1 mg/kg to about 8 mg/kg, 0.1 mg/kg to about 5 mg/kg, 0.5 mg/kg to about 10 mg/kg, 1 mg/kg to about 10 mg/kg, 1.5 mg/kg to about 10 mg/kg and 2 mg/kg to about 10 mg/kg. Specific dosages of BCAT1 inhibitors in formulations include: 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5 mg/kg, 6 mg/kg, 7 mg/kg, 8 mg/kg, 9 mg/kg, and 10 mg/kg. However, the amount of BCAT1 inhibitor in formulations administered to a subject will vary between wide limits, depending upon the location, source, identity, extent and severity of the disorder or disease, the age and condition of the individual to be treated, etc. A physician will ultimately determine appropriate dosages to be used. Administration frequencies of formulations comprising one or more BCAT1 inhibitors will also vary depending on factors that include the disease or condition being treated and the modes of administration. Each formulation may be independently administered 4, 3, 2 times or once daily, every other day, every third day, every fourth day, every fifth day, every sixth day, once weekly, every eight days, every nine days, every ten days, bi-weekly, monthly and bi-monthly.

The invention is further understood by the following non-limiting examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

II. Suitable Methods for Practicing the Invention

Synthesis of Compound (3)

Compound (3) can be synthesized according to the schematic below. Reactants (16) and (17) are either commercially available or can generally be prepared by conventional techniques known to those skilled in the art.

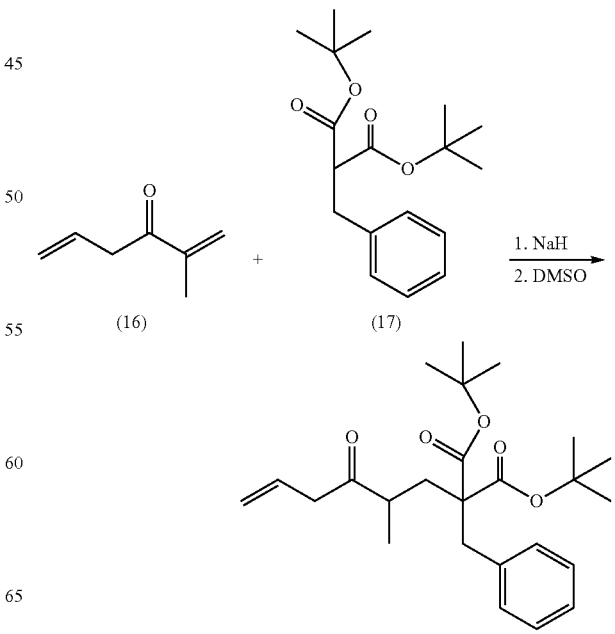

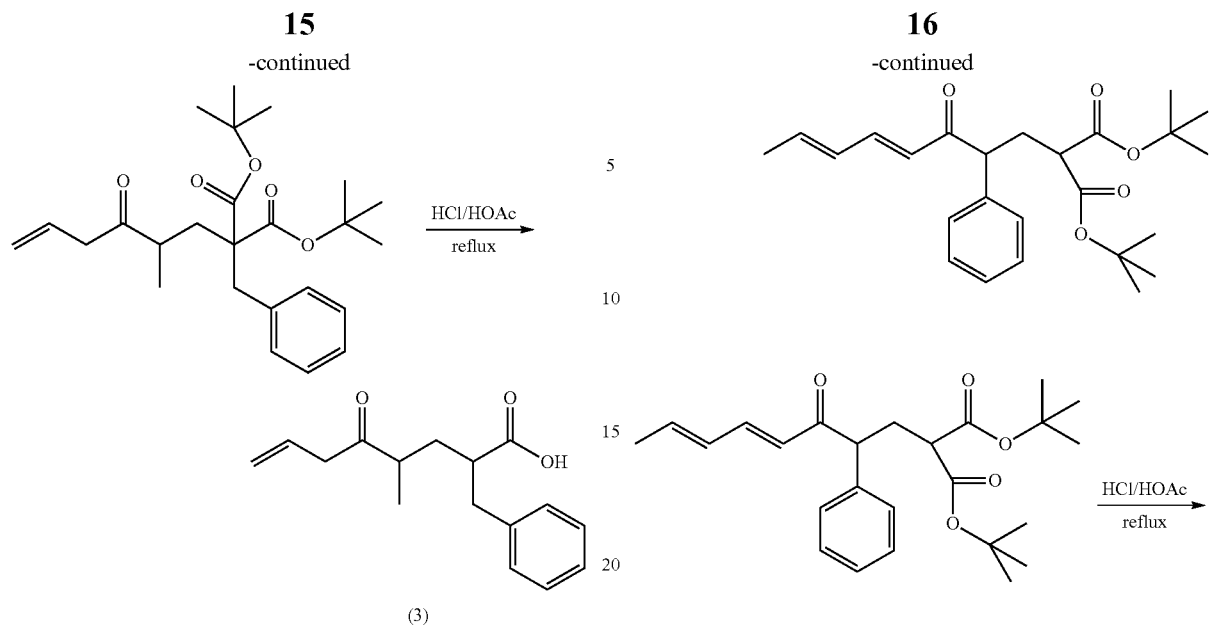

Synthesis of Compound (4)

Compound (4) can be synthesized according to the schematic below. Reactants (18), (19), and (20) are either commercially available or can generally be prepared by conventional techniques known to those skilled in the art.

Synthesis of Compound (5)

Compound (5) can be synthesized according to the schematic below. Reactants (21), (22), and (23) are either commercially available or can generally be prepared by conventional techniques known to those skilled in the art.

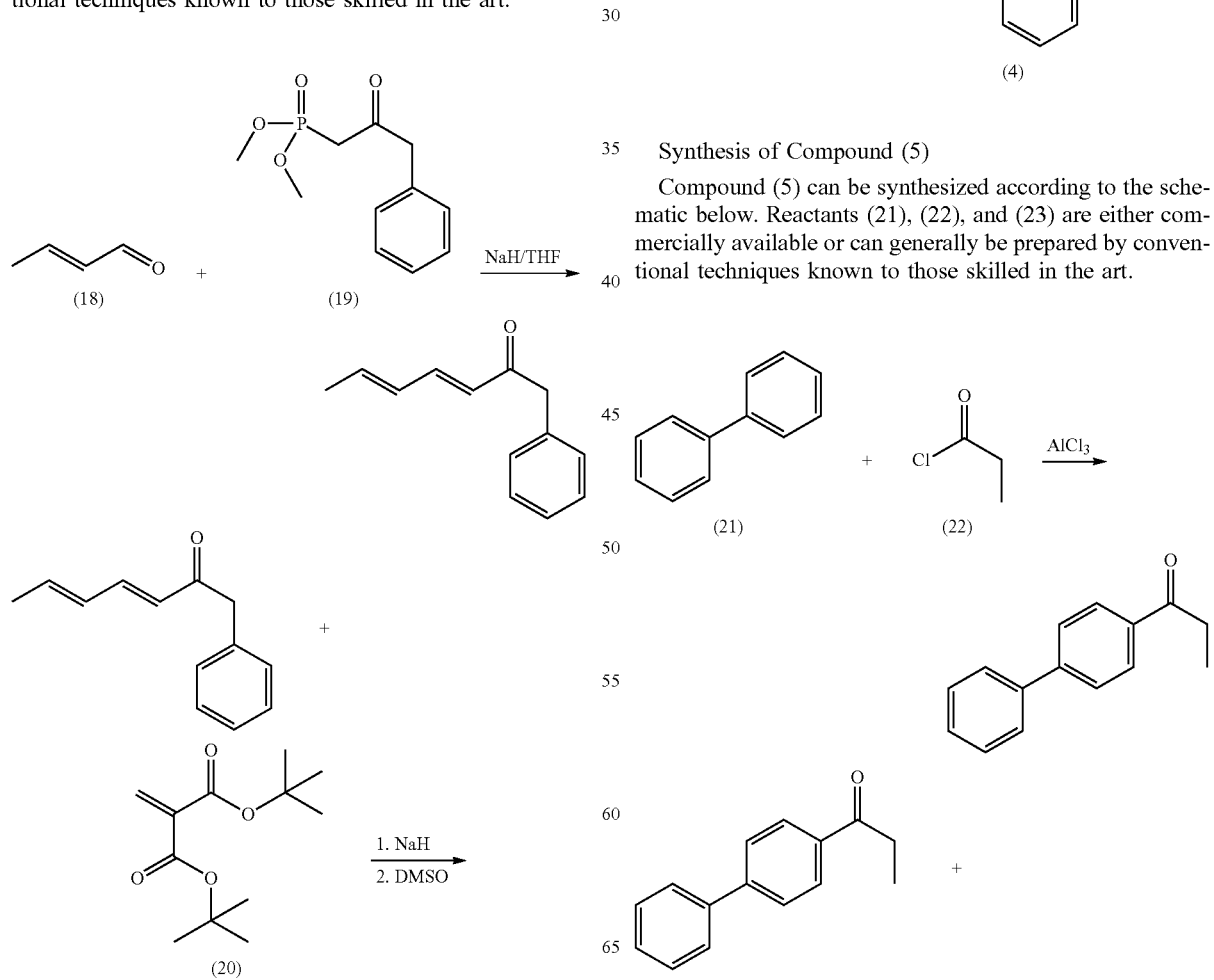

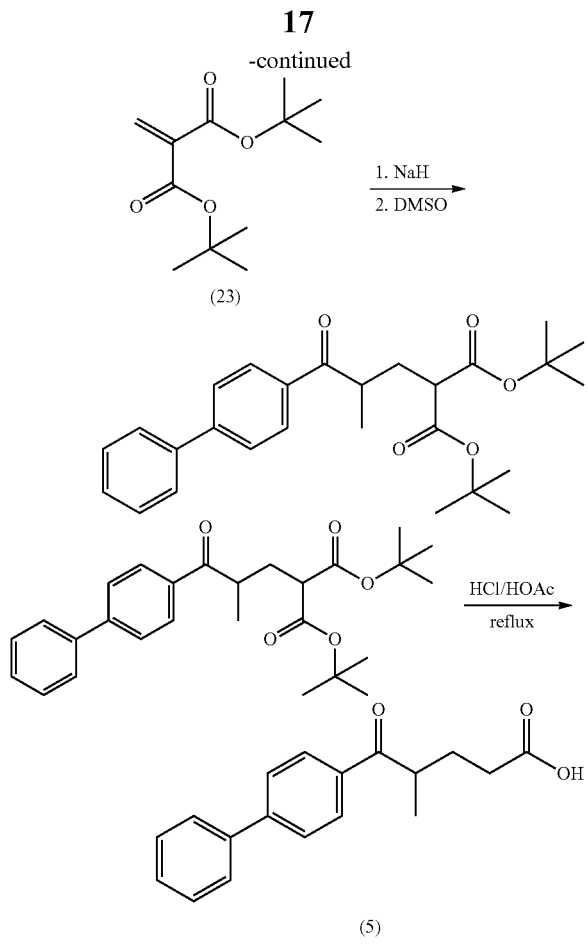

In Vitro Tumor Cell Proliferation Assay

The ability of a BCAT1 inhibitor to suppress cancer growth is evaluated in vitro using a cell proliferation assay. A cell proliferation assay typically involves the routine culturing of a cell line to near confluency in the appropriate media. Subsequently, the cells are trypsinized and plated on a 96-well plate at 2,000 or 5,000 cell per well. The cells are cultured for 48 to 96 hours in the presence or absence of the inhibitor. Cell proliferation is then determined using spectrophotometry (MTT assay, BrdU assay) or fluorimetry (Cyquant assay).

In Vitro Fibrosis Assay

In vitro fibrosis is assessed by measuring collagen synthesis after treatment of fibroblast cells with a profibrotic stimuli such as TGF-$\beta_1$ or bleomycin. Collagen secretion into the media can be quantified in conditioned media using an appropriate ELISA kit.

Activation of Synovial Cells

Rheumatoid arthritis (RA) pathology is associated with the sustained activation of synovial cells to produce pro-inflammatory proteins. Anti-rheumatic agents are tested in vitro for their ability to inhibit secretion of pro-inflammatory proteins from macrophages and fibroblasts in the presence of an inflammatory stimulus such as LPS. At the end of the experiment, secretory proteins are detected in the conditioned media of the cells via an immunological assay such as ELISA or Western immunoblotting.

CIA Model

Collagen Induced Arthritis (CIA) is a well-known animal inflammation model of RA (Brand D. et al, Collagen-induced arthritis, Nature Protocols 2007, 2:1269-1275) In this model, joint arthritis is induced in rats or mice through immunization with heterologous type II collagen in adjuvant and clinically manifested by the presence of erythema and edema in the extremities of the animals. Commonly, anti-rheumatic agents are administered at the onset of arthritis or upon clinical manifestation. During the experiment, the animals are scored for the presence of arthritis.

In Vivo Fibrosis Assay

Pulmonary fibrosis is assessed after intratracheal administration of 1 mg/kg bleomycin. Therapy with an antifibrotic agent commonly starts at day 0 after bleomycin administration; the experiment is terminated 14 days later. Lung fibrosis is evaluated biochemically (determination of collagen content in homogenized lung using the Sircol Assay (Lareu R. et al, Essential modification of the Sircol Collagen Assay for the accurate quantification of collagen content in complex protein solutions, Acta Biomaterialia 2010, 6(8): 3146-51), histologically (determination of collagen deposition by Trichrome Masson (TM) staining), and cytologically by differential leukocyte count in bronchoalveolar lavage fluid.

Example 1

Synthesis of Compound (2)

Compound (2) was synthesized according to the schematic below. Reactants (24) and (25) were commercially available materials. $^1$H NMR (400 MHz, CDCl$_3$): 2.625; (4, 1H, quint), 2.870; (5, 2H, d), 1.740; (6, 2H, t), 2.468; (8, 1H, tq,), 7.245 (9, 1H, d), 7.245; (10, 1H, d), 1.069; (12, 3H, d), 7.276; (13, 1H, d), 7.276; (14, 1H, d), 2.151 (16, 3H), 7.232; (17, 1H, t) 1H), 2.45-2.53; (m, 1H), 5.95-6.00; (m, 1H), 7.33-7.42; (m, 5H).

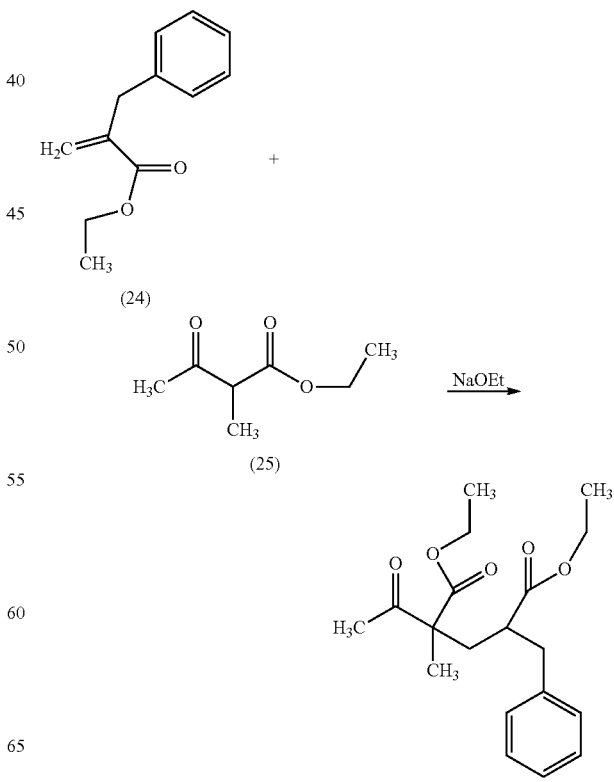

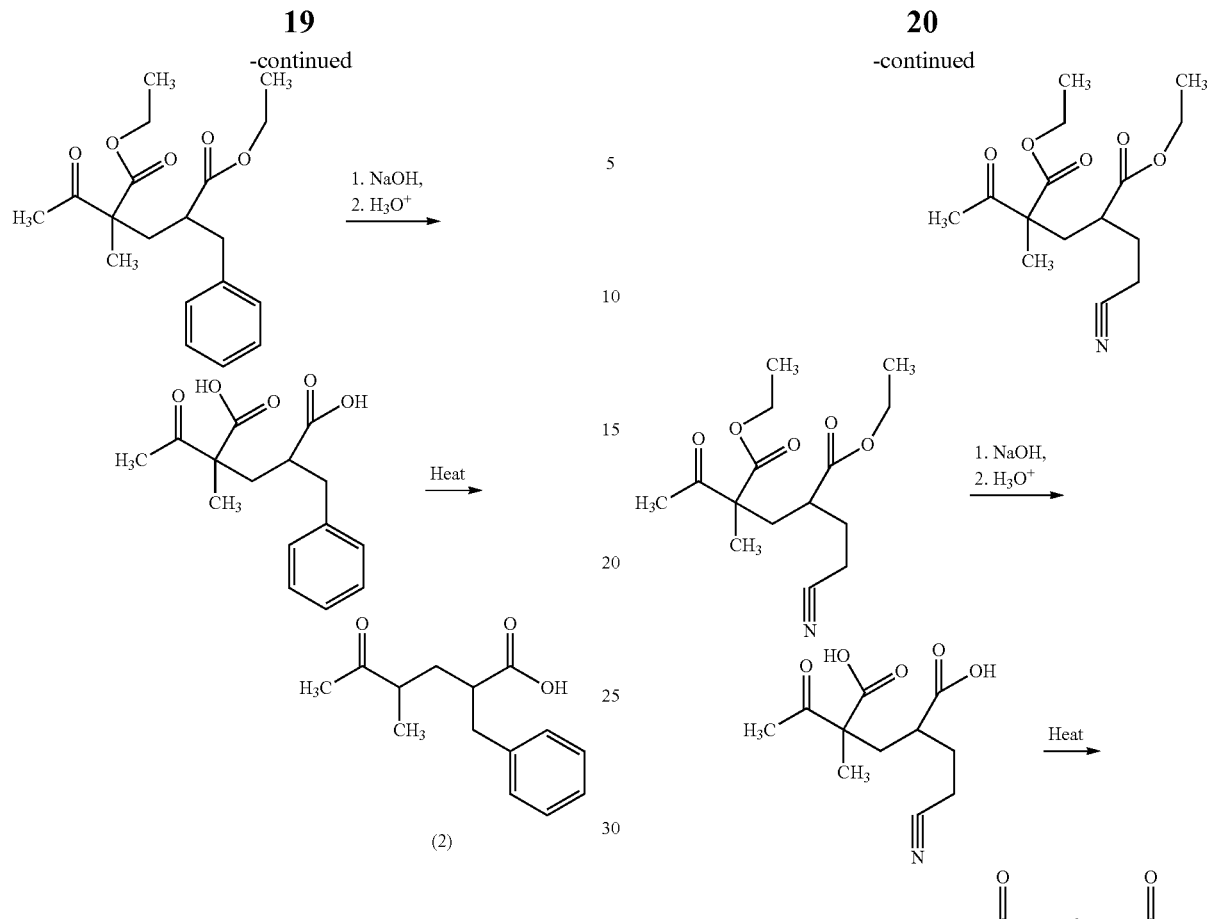

Example 2

Synthesis of Compound (8)

Compound (8) was synthesized according to the schematic below. Reactants (26) and (27) were commercially available materials. $^1$H NMR (400 MHz, CDCl$_3$): 2.439; (4, 1H, quint), 1.715; (5, 2H, d), 1.857; (6, 2H, dt), 2.451; (7, 1H, tq), 2.793; (8, 2H, t), 1.101; (10, 3H, d), 2.149; (13, 3H)

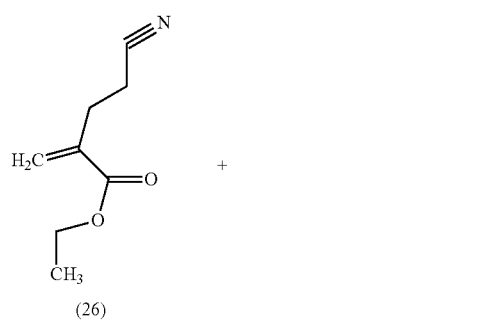

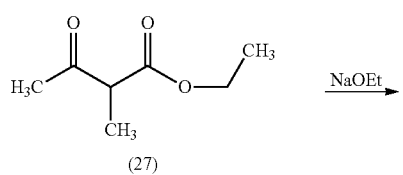

Example 3

Expression of BCAT1 in TGF-β$_1$-Stimulated Fibroblasts

Human fibroblasts were plated onto 35 mm culture dishes and incubated until they reached confluency. They were then treated with 7 ng/mL TGF-β$_1$ for 48 hrs. Cell lysates were collected and analyzed for the presence of BCAT1 by Western Immunoblotting. The experiment was repeated four times. FIG. 1.A shows BCAT1 expression levels in unstimulated [TGF-β$_1$(−)] and TGF-β$_1$-stimulated [TGF-β$_1$(+)] cells. FIG. 1B shows the normalized BCAT1 expression levels from 4 experiments. FIG. 1B indicates that TGF-β$_1$ stimulation of fibroblasts leads to 3-fold increase in the expression of BCAT1.

Example 4

Inhibition of BCAT1 Enzymatic Activity by Compounds 2, 7 and 8

The ability of the compounds of the invention to inhibit BCAT1 enzymatic activity was confirmed spectrophotometrically. In this experiment, 0.2 to 0.5 μg of recombinant human BCAT1 from Abcam was added to 95 μL of a reaction buffer containing 5 μL pyridoxal 5'-phosphate (PLP), 50 mM ammonium sulfate, 0.05 mM NADH, 5 mM DTT, 5 mM a-ketoglutarate, 10 mM leucine, and 0.95 U leucine dehydrogenase (EMD Chemicals) and various concentrations of compounds 2, 7 and 8. Addition of BCAT1 to the reaction mixture led to the consumption of NADH, which was measured fluorometrically (ex:330-370 nm; em:450 nm). The rate of change of fluorescence was then estimated over of period of 10 min (10 cycles; 1 cycle/min). The assay was performed in triplicate in a 96-well plate. In Table 1, the results were expressed as % Control Enzymatic Activity, which is defined as the BCAT1 activity observed in the reaction mixture in the absence of an inhibitor. Table 1 shows that compounds 2, 7, and 8 are able to inhibit the enzymatic activity of BCAT1 with an $IC_{50}$ value ranging from 0.5 to 50 nM.

TABLE 1

| Concentration (nM) | % Control Enzymatic Activity | | |
|---|---|---|---|
| | Structure 2 | Structure 7 | Structure 8 |
| 0.5 | ND | ND | 47 |
| 1 | 86 | 67 | ND |
| 10 | 71 | 0 | 23 |
| 100 | 28 | 0 | 16 |

ND: Not Done

Example 5

Confluent monolayers of human fibroblasts, plated onto duplicate 35 mm dishes, were pretreated with various concentrations of compounds 2, 6, and 7 for 30 min followed by stimulation of the cells with 7 ng/mL TGF-$\beta_1$ for 48 hrs. At the end of the experiment, conditioned media were collected and assessed for the presence of secreted collagen I, whereas cells were collected and lysed. Collagen I secretion was quantified using an ELISA kit from R&D Systems per the manufacturer's instructions and expressed as arbitrary absorbance units per μg of cell lysate. In Table 2, results are shown as % Control Collagen Production, defined as the amount of collagen I secreted per μg of cell lysate from fibroblast cultures stimulated with TGF-$\beta_1$ in the absence of an inhibitor. Table 2 indicates that compounds 2, 6, and 7 completely inhibit collagen I secretion at a concentration of 5-10 mM.

TABLE 2

| Concentration (mM) | % Control Collagen Production | | |
|---|---|---|---|
| | Structure 2 | Structure 6 | Structure 7 |
| 2 | 111 | 105 | 150 |
| 5 | 4 | 77 | 41 |
| 10 | ND | 2 | 2 |

What is claimed is:
1. A compound of Formula (1):

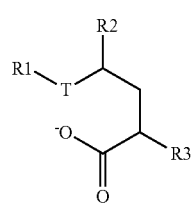

or a pharmaceutically acceptable salt of the compound, wherein:
T is —C(=O)—;
R1 is a phenyl group substituted with one substituent selected from the group consisting of halo, CN, —COOH, —NH$_2$, —NH(CH$_3$), —N(CH$_3$)$_2$, and —CONH$_2$, and optionally further substituted with one or more substituents selected from the group consisting of —C$_1$-C$_6$ alkyl, halo, —OH, alkoxy, —NH$_2$, —COOH, —NH(CH$_3$), —N(CH$_3$)$_2$, and —CONH$_2$;
R2 is a phenyl, optionally substituted with one or more substituents selected from the group consisting of —C$_1$-C$_2$ alkyl, halo, CN, —COOH, —OH, alkoxy, —NH$_2$, —COOH, —NH(CH$_3$), —N(CH$_3$)$_2$, and —CONH$_2$; and
R3 is hydrogen.

2. A compound of Formula (1),

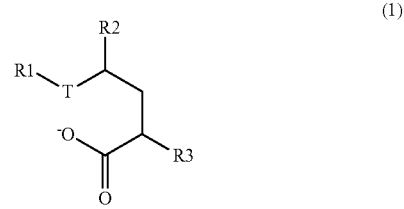

or an N-oxide thereof, or a pharmaceutically acceptable salt of the compound or N-oxide,
where T is —C(=O)—,
where R1 is CH$_3$, R2 is —CH$_3$, and R3 is —(CH$_2$)$_2$CN, having the structure (8)

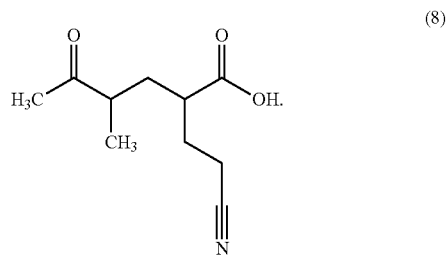

3. The compound of claim 1, or an N-oxide thereof, or a pharmaceutically acceptable salt of the compound or N-oxide, where R1 is 4-bromo-phenyl, R2 is phenyl, and R3 is hydrogen, having the structure

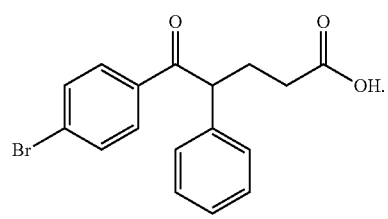 [SMILES: O=C(O)CCC(C(=O)c1ccc(Br)cc1)c1ccccc1]

4. The compound of claim 1 or an N-oxide thereof, or a pharmaceutically acceptable salt of the compound or N-oxide, where R1 is 4-bromo-phenyl, R2 is 4-chloro-phenyl, and R3 is hydrogen, having the structure

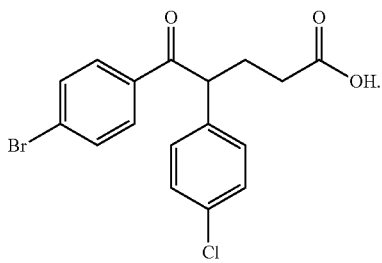 [SMILES: O=C(O)CCC(C(=O)c1ccc(Br)cc1)c1ccc(Cl)cc1]

5. A compound of Formula (1),

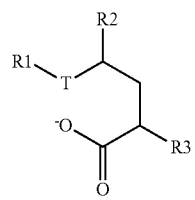 (1)

or an N-oxide thereof, or a pharmaceutically acceptable salt of the compound or N-oxide, where T is —C(=O)—, where R1 is (a-3), where X is —N or —CH, and R4, R5, R6, and R7 are independently H or —CH$_3$,

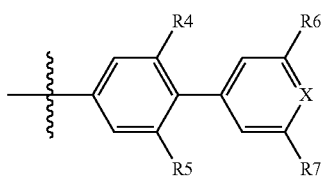 (a-3)

where R2 is a phenyl group, optionally substituted with one or more substituents selected from the group consisting of —C$_1$-C$_2$ alkyl, halo, CN, —COOH, —OH, —C$_1$-C$_2$ alkoxy, —NH$_2$, —COOH, —NH(CH$_3$), —N(CH$_3$)$_2$, and —CONH$_2$; and where R3 is hydrogen.

6. The compound of claim 5 or an N-oxide thereof, or a pharmaceutically acceptable salt of the compound or N-oxide, where R1 is 4-(4-pyridyl)phenyl, R2 is phenyl, and R3 is hydrogen, having the structure

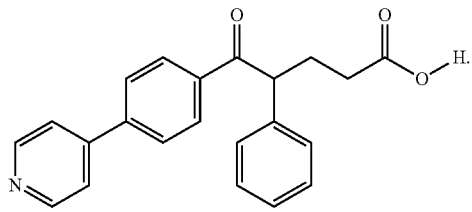

7. The compound of claim 1 or an N-oxide thereof, or a pharmaceutically acceptable salt of the compound or N-oxide, where R1 is 4-bromo-2,6-phenyl, R2 is phenyl, and R3 is hydrogen, having the structure

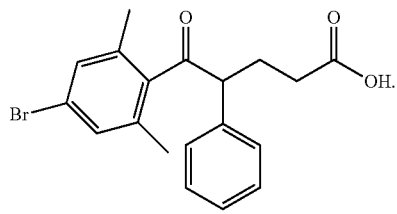 [SMILES: Cc1cc(Br)cc(C)c1C(=O)C(CCC(=O)O)c1ccccc1]

8. The compound of claim 1, or an N-oxide thereof, or a pharmaceutically acceptable salt of the compound or N-oxide, where R1 is 4-bromo-phenyl, R2 is 3,5-dimethyl-phenyl, and R3 is hydrogen, having the structure

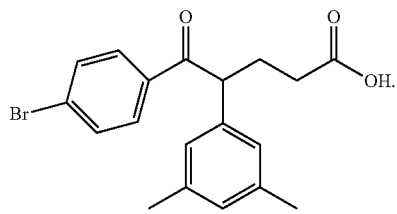 [SMILES: Cc1cc(C)cc(C(CCC(=O)O)C(=O)c2ccc(Br)cc2)c1]

* * * * *